United States Patent
Vendely et al.

(10) Patent No.: US 10,575,850 B2
(45) Date of Patent: Mar. 3, 2020

(54) SYSTEMS FOR RELEASE OF ADJUNCT IN A SURGICAL STAPLING DEVICE

(71) Applicant: Ethicon LLC, Guaynabo, PR (US)

(72) Inventors: Michael J. Vendely, Lebanon, OH (US); Prudence Vulhop, Cincinnati, OH (US); Jason L. Harris, Lebanon, OH (US); Frederick E. Shelton, IV, Hillsboro, OH (US); David C. Yates, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 353 days.

(21) Appl. No.: 15/436,072

(22) Filed: Feb. 17, 2017

(65) Prior Publication Data
US 2018/0235623 A1  Aug. 23, 2018

(51) Int. Cl.
*A61B 17/072* (2006.01)
*A61B 17/115* (2006.01)

(52) U.S. Cl.
CPC .... *A61B 17/07207* (2013.01); *A61B 17/1155* (2013.01); *A61B 2017/07271* (2013.01); *A61B 2017/07278* (2013.01); *A61B 2017/07285* (2013.01)

(58) Field of Classification Search
CPC .......................................... A61B 2017/07278; A61B 2017/07285; A61B 17/07207; A61B 2017/07271; A61B 17/07292; A61B 17/1155
USPC ..................... 606/143, 219; 227/175.1–182.1
See application file for complete search history.

(56) References Cited

U.S. PATENT DOCUMENTS

| | | | |
|---|---|---|---|
| 6,273,897 B1 * | 8/2001 | Dalessandro | .... A61B 17/07207 606/139 |
| 7,143,925 B2 | 12/2006 | Shelton, IV et al. | |
| 7,601,118 B2 | 10/2009 | Smith et al. | |
| 8,317,070 B2 | 11/2012 | Hueil et al. | |
| 8,393,514 B2 | 3/2013 | Shelton, IV et al. | |

(Continued)

FOREIGN PATENT DOCUMENTS

EP        2245993 A2    11/2010
WO   WO-2016073538 A1    5/2016

OTHER PUBLICATIONS

Extended European Search Report for EP App. No. 18157185.2 dated Apr. 24, 2018 (8 pages).

(Continued)

*Primary Examiner* — Robert F Long
*Assistant Examiner* — Xavier A Madison
(74) *Attorney, Agent, or Firm* — Mintz Levin Cohn Ferris Glosky and Popeo, P.C.

(57) ABSTRACT

Systems and methods for separating an adjunct from a jaw of an end effector of a surgical stapling device are provided. The end effector, including first and second jaws configured to clamp tissue therebetween, include an adjunct material releasably retained on at least one of the jaws. The end effector also includes a firing bar configured to move between an unfired position at a proximal end of the end effector and a fired position at a distal end of the end effector. An adjunct removal assembly that can reside in the jaw is configured to couple to and move with the firing bar to separate the adjunct material from the surgical stapling device as the firing bar having the adjunct removal assembly coupled thereto is returned from the fired position to the unfired position.

13 Claims, 8 Drawing Sheets

(56) References Cited

U.S. PATENT DOCUMENTS

| | | |
|---|---|---|
| 9,282,962 B2 | 3/2016 | Schmid et al. |
| 2013/0221065 A1 | 8/2013 | Aronhalt et al. |
| 2013/0256377 A1 | 10/2013 | Schmid et al. |
| 2014/0103093 A1* | 4/2014 | Koch, Jr. ......... A61B 17/07207 227/180.1 |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0272575 A1 | 10/2015 | Leimbach et al. |
| 2015/0277471 A1 | 10/2015 | Leimbach et al. |
| 2015/0351758 A1 | 12/2015 | Shelton, IV et al. |
| 2016/0089142 A1 | 3/2016 | Harris et al. |
| 2017/0055986 A1 | 3/2017 | Harris et al. |

OTHER PUBLICATIONS

U.S. Appl. No. 15/436,183 entitled "Hybrid Mechanism for Attachment of an Adjunct to a Surgical Instrument" filed Feb. 17, 2017.
U.S. Appl. No. 15/436,328 entitled "Systems for Coupling Adjuncts to an End Effector" filed Feb. 17, 2017.

* cited by examiner

SYSTEMS FOR RELEASE OF ADJUNCT IN A SURGICAL STAPLING DEVICE

FIELD

The present disclosure relates generally to adjunct materials used in conjunction with an end effector of a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as-well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

A surgical stapling device includes a first jaw having a cartridge with a plurality of staple cavities configured to seat staples therein. The staple cavities open on a tissue-facing surface of the cartridge. The surgical stapling device includes a second jaw opposing the first jaw and having an anvil with a plurality of staple forming cavities formed on a tissue-facing surface thereof. The first and second jaws are configured to clamp tissue therebetween. The surgical stapling device also includes an adjunct material releasably retained on at least one of the first and second jaws. The surgical stapling device further includes a firing bar configured to move between an unfired position at a proximal end of the end effector and a fired position at a distal end of the end effector, and an adjunct removal assembly configured to couple to and move with the firing bar to separate the adjunct material from the surgical stapling device as the firing bar having the adjunct removal assembly coupled thereto is returned from the fired position to the unfired position.

The surgical stapling device can vary in many ways. In one embodiment, the firing bar includes at least one of a knife and a staple driving assembly configured to cause the staples to fire from the staple cavities against the staple forming cavities. In another embodiment, the adjunct removal assembly is disposed at the distal end of the end effector in a configuration in which it is not coupled to the firing bar when the surgical stapling device is in a pre-fired configuration.

In one embodiment, the adjunct removal assembly is configured to move longitudinally along a knife channel in the cartridge. In another embodiment, the firing bar includes a first mating feature. The adjunct removal assembly includes an adjunct removal feature and a second mating feature configured to mate with the first mating feature when the firing bar is actuated to achieve the firing position. The adjunct removal assembly is configured to move with the firing bar when the second mating feature is mated with the first mating feature such that, as the adjunct removal assembly is moved with the firing bar, the adjunct removal feature separates the adjunct material from one of the first and second jaws.

In one embodiment, the adjunct removal assembly is operably associated with the cartridge. In another embodiment, the adjunct removal feature comprises a plate configured to slide between the adjunct material and one of the first jaw and the second jaw. In another embodiment, the first mating feature comprises a cavity in the firing bar. In yet another embodiment, the second mating feature comprises at least one protrusion configured to mate with the cavity in the firing bar. In another embodiment, the at least one protrusion comprises a pair of bars disposed such that the firing bar sits between the bars when the adjunct removal assembly is coupled to and moves with the firing bar.

A surgical method includes actuating a firing bar of an end effector. The firing bar of the end effector includes a first jaw having a cartridge with a plurality of staple cavities configured to seat staples therein and a second jaw opposing the first jaw and having an anvil with a plurality of staple forming cavities formed on a tissue-facing surface thereof. The first and second jaws are configured to clamp tissue therebetween. The firing bar is actuated so as to be moved from an unfired position at a proximal end of the end effector to a fired position in a distal end of the end effector. The surgical method also includes engaging an adjunct removal assembly of the end effector with the firing bar when the firing bar is in the fired position. The surgical method further includes actuating the firing bar to return it from the fired position to the unfired position such that, as the firing bar is actuated to return to the unfired position, the adjunct removal assembly is moved with the fired bar and thereby causes an adjunct material releasably retained on at least one of the first and second jaws to be separated from the at least one jaw.

In one implementation of the method, the firing bar includes at least one of a knife and a staple driving assembly configured to cause the staples to fire from the staple cavities against the staple forming cavities. In another implementation of the method, the adjunct removal assembly is disposed at the distal end of the end effector in a configuration in which it is not coupled to the firing bar when the surgical stapling device is in a pre-fired configuration.

In one implementation of the method, the firing bar includes a first mating feature, and engaging the adjunct removal assembly of the end effector with the firing bar comprises engaging a second mating feature of the adjunct removal assembly with the first mating feature. In another implementation of the method, the adjunct removal assembly is configured to move longitudinally along a knife channel in the cartridge.

BRIEF DESCRIPTION OF DRAWINGS

This invention will be more fully understood from the following detailed description taken in conjunction with the accompanying drawings, in which.

DETAILED DESCRIPTION

Figure 1:
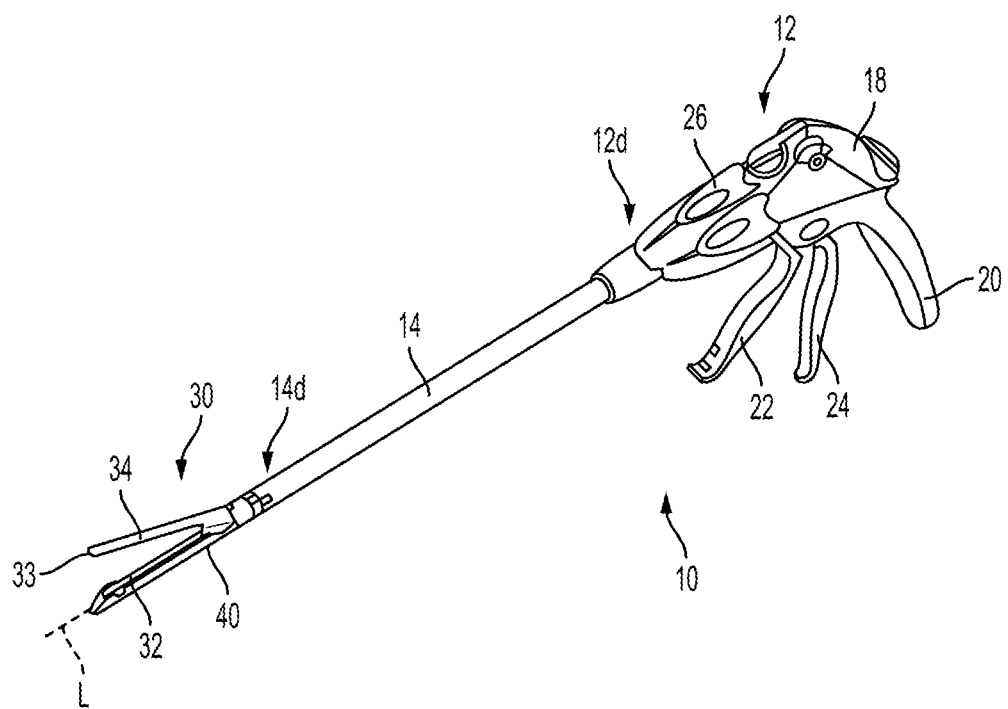
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example, linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used on a variety of tissues in a variety of different surgical procedures, for example in thoracic surgery or in gastric surgery.

Figure 2:
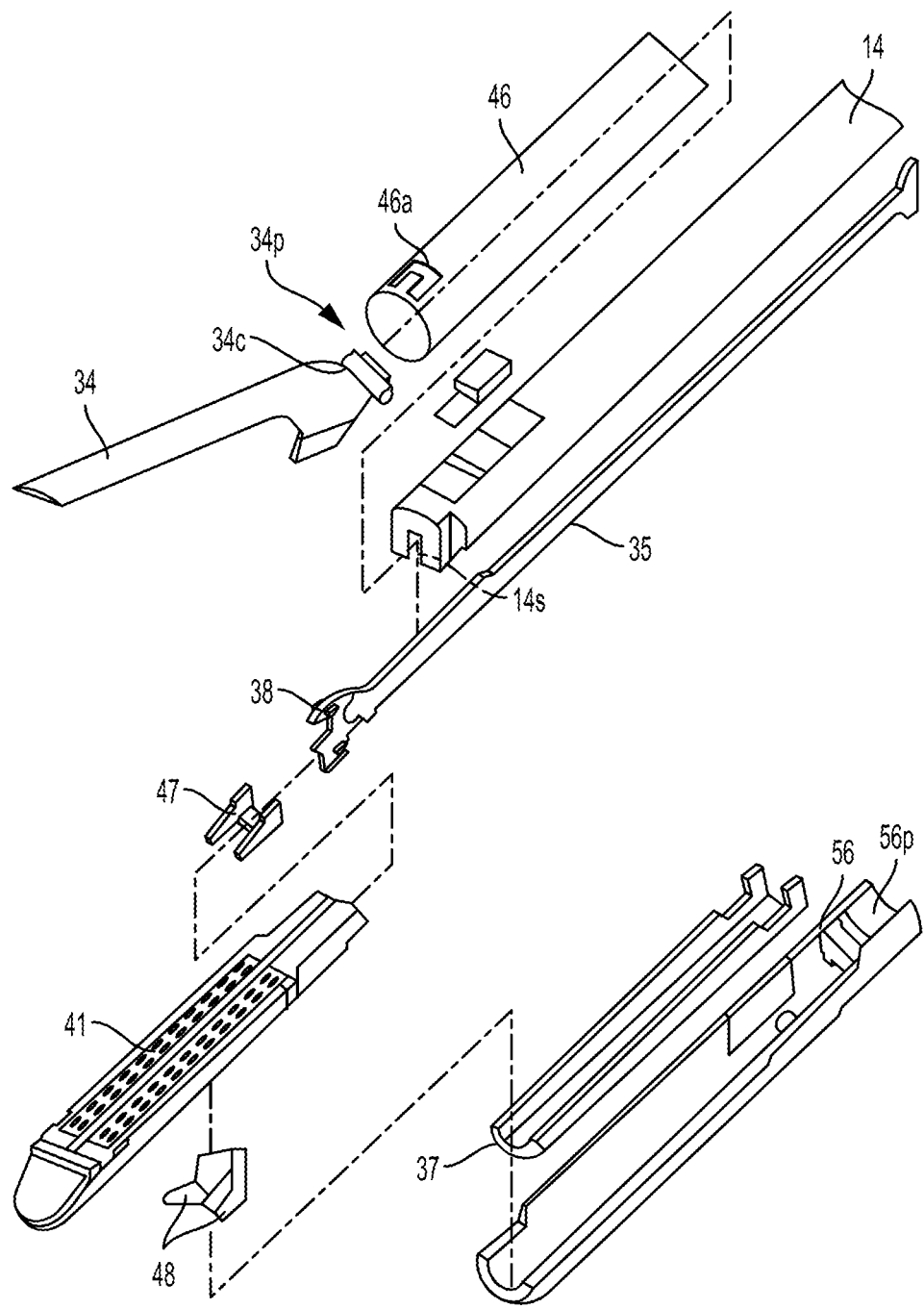
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
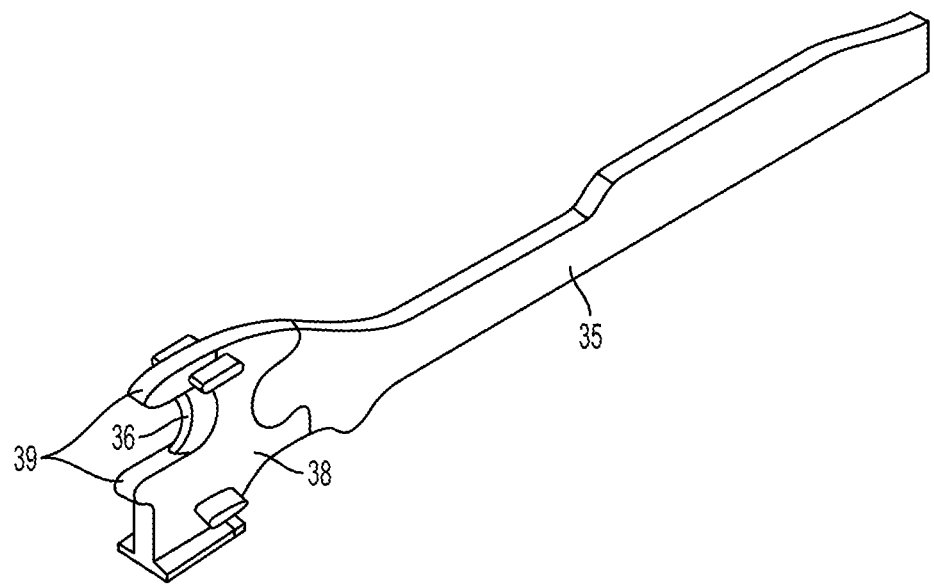
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
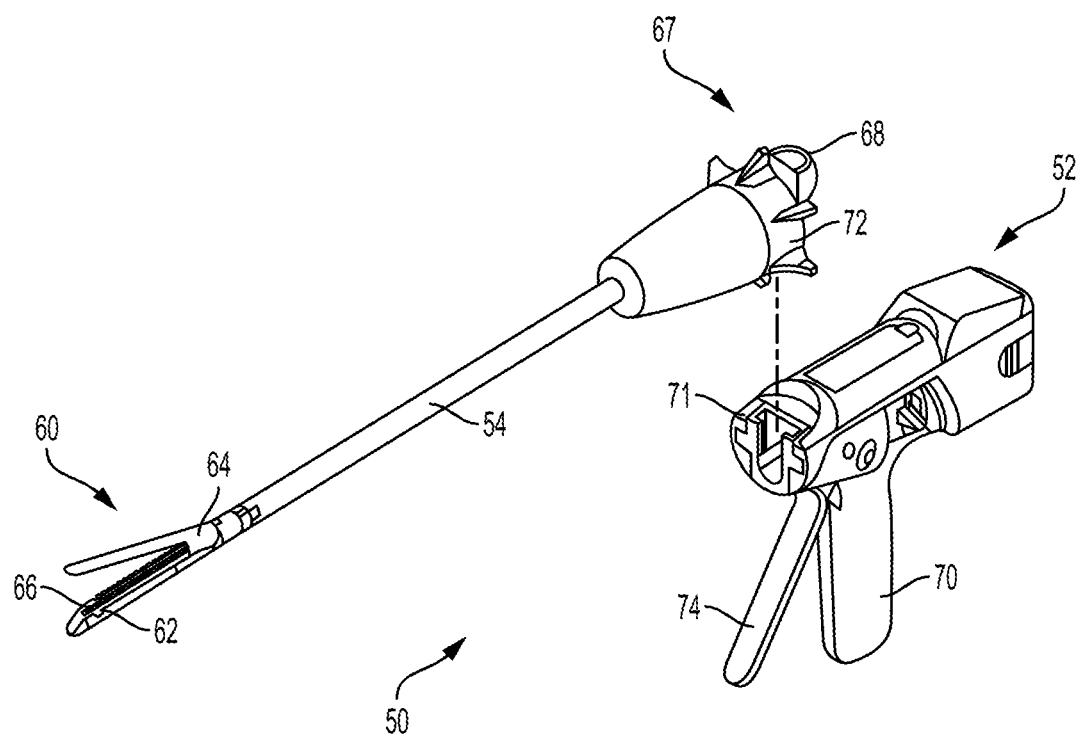
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
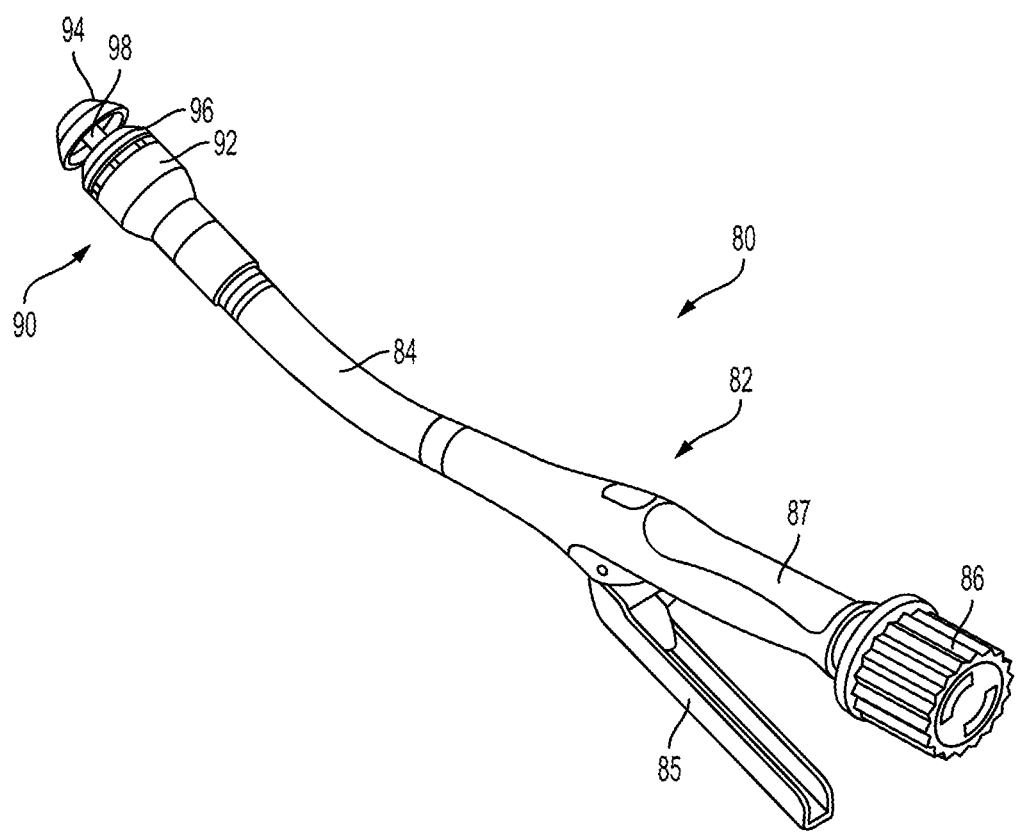
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be made from a film formed from any suitable material or a combination of materials discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct. The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjuncts that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Implementation

Various exemplary devices, systems and methods for release of adjunct in a surgical stapling device are described herein.

Implantable adjuncts can be releasably attached to a jaw of an end effector of a surgical stapling device. The coupling can be done in various ways, for example, adhesives and/or adhesive features can be used to couple the adjunct to a surface of the jaw. This can allow manipulating the end effector with the adjunct during a surgical procedure, while the adjunct is prevented from being prematurely separated from the surface of the jaw before the adjunct is stapled to a tissue. After the adjunct has been stapled to the tissue, the adjunct can be detached from the jaw by a force exerted by the tissue (e.g., shearing force, pull, etc.). Attaching systems (e.g., those using polydioxanone adhesives) that attach the adjunct to the surface of the jaw in a secure (strong) manner can be advantageous as they ensure that the adjunct does not slip or slide off the jaw's surface prior to the stapling to the tissue. A strong attachment however can make the adjunct removal process challenging. This challenge can be obviated by including an adjunct removal mechanism or assembly in a jaw of the surgical stapling device that is configured to separate the adjunct from the jaw.

Accordingly, an adjunct removal mechanism can be configured to detach the adjunct from the surface of the jaw of the surgical stapler device after the adjunct has been stapled to the tissue. This can be done for example, by using a motion of a firing bar (in the surgical stapling device) from a fired position at the distal end of the end effector to an unfired position at the proximal end of the end effector. The firing bar can couple to the adjunct removal mechanism at the distal end, and return back to the proximal end (i.e., unfired position) with the adjunct removal mechanism. The adjunct removal mechanism can include an adjunct removal feature that separates the adjunct from the jaw of the surgical stapler device as the adjunct removal mechanism moves from the distal to the proximal end.

Figure 6A:
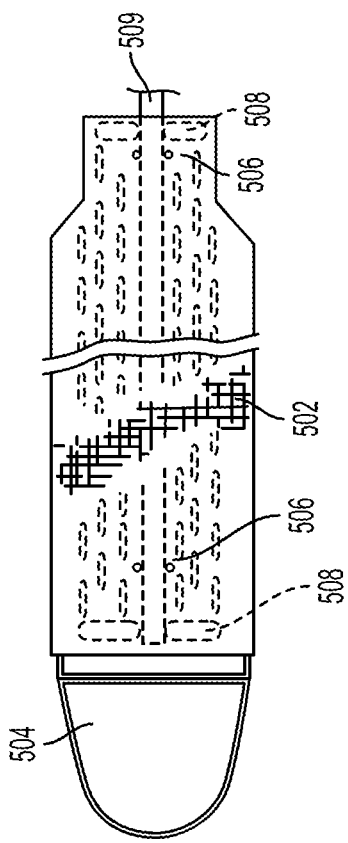
FIG. 6A illustrates an example of an adjunct releasably retained to a tissue facing surface of a surgical stapler device.

FIG. 6A illustrates an example of an adjunct 502 releasably retained to a tissue facing surface of a lower jaw 504 of an end effector of a surgical stapler device. One or more portions of the adjunct 502 can be attached to the lower jaw 504 by an adhesive 508. The adhesive 508 can be disposed at any suitable pattern—for example, it can be distributed between the adjunct 502 and lower jaw 504 at distal and proximal ends of the adjunct 502, as shown in FIG. 6A. The adhesive can be, for example, a pressure sensitive adhesive (PSA). Additionally or alternately, a second adhesive, for example, cyanoacrylate (CA), can attach the adjunct 502 to the tissue facing surface of the lower jaw 504. For example, as shown in FIG. 6A, one or more portions of the adjunct 502 can be coupled to the jaw 504 via attachment portions or points 506 formed from the second adhesive. It should be appreciated, however, that the first and second adhesives can be the same material (e.g., a PSA, CA, etc.), or a combination of suitable materials. The adjunct 502 can be attached to the lower jaw 504 by various mechanisms, for example, as described in U.S. patent application Ser. No. 15/436,183, entitled "Hybrid Mechanism for Attachment of an Adjunct to a Surgical Instrument" filed on Feb. 17, 2017, the entire content of which is incorporated herein by reference.

As shown in FIG. 6A, the lower jaw 504 includes a knife channel 509 that extends longitudinally along the length of the lower jaw 504. The attachment points 506 of the second adhesive (or any other adhesive) can be distributed, for example, along and/or around the knife channel 509. It should be appreciated however that four attachment points 506 are shown by way of example only, as any suitable number of attachment points can be formed at any desired pattern(s). Further, in some embodiments, the attachment points, which can be configured to be broken by a suitable release mechanism, can be formed at areas at which the adjunct was heated and pressed onto the jaw and allowed to cool and thus conform to the geometry of the jaw. In this way, one or more portions of the adjunct mechanically "grip" the jaw (in some cases, in certain textured or roughened portions of the jaw).

Figure 6C:
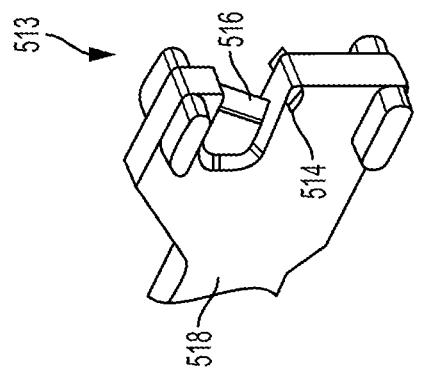
FIG. 6C illustrates a perspective view of an embodiment of a distal end of a firing bar of the surgical stapler device.
Figure 6B:
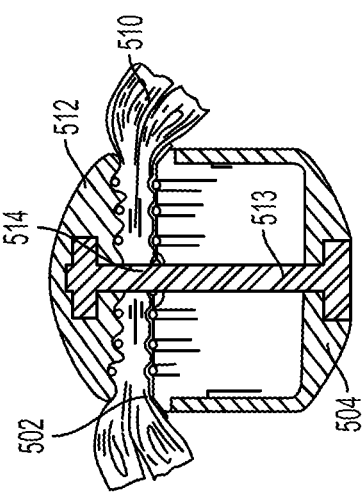
FIG. 6B illustrates a cross-sectional view of a tissue clamped between an upper jaw and a lower jaw of the surgical stapler device.

FIG. 6B illustrates the surgical stapler device clamping on a tissue 510. The tissue 510 is clamped between an upper jaw 512 and the lower jaw 504 of the stapler. The adjunct 502 lies between the tissue 510, and the tissue facing surface of the lower jaw 504. Due to the adjunct 502, portions of the tissue facing surface do not come in direct contact with the tissue 510. A distal end 513 of a firing bar 518 (e.g., an I-Beam, an E-Beam, or otherwise configured end) extends vertically with respect to the tissue facing surface. The distal end 513 includes flanges 514 configured to scrape the adjunct 502 from the tissue-facing surface of the lower jaw 504. For example, the flange 514 can cause adhesive 506 to crack and thereby release portions of the adjunct 502 when the firing bar 518 moves from the proximal to the distal end or vice-versa. The flanges 514 are shown as having slanted surfaces by way of example, and they can have other configurations.

FIG. 6C illustrates a perspective view of an embodiment of the distal end 513 of the firing bar 518. The distal end 513 includes a knife 516 and the flange 514. As the distal end 513 travels from a proximal end to a distal end of the stapler, the knife 516 cut the tissue 510.

FIGS. 6A-6C illustrate that a knife of a firing bar assembly can be used to separate an adjunct from a jaw which has the adjunct releasably coupled thereto. In some embodiments, assemblies having other configurations can be used to separate an adjunct from a jaw of an end effector in conjunction with movement of the firing bar.

Figure 7A:
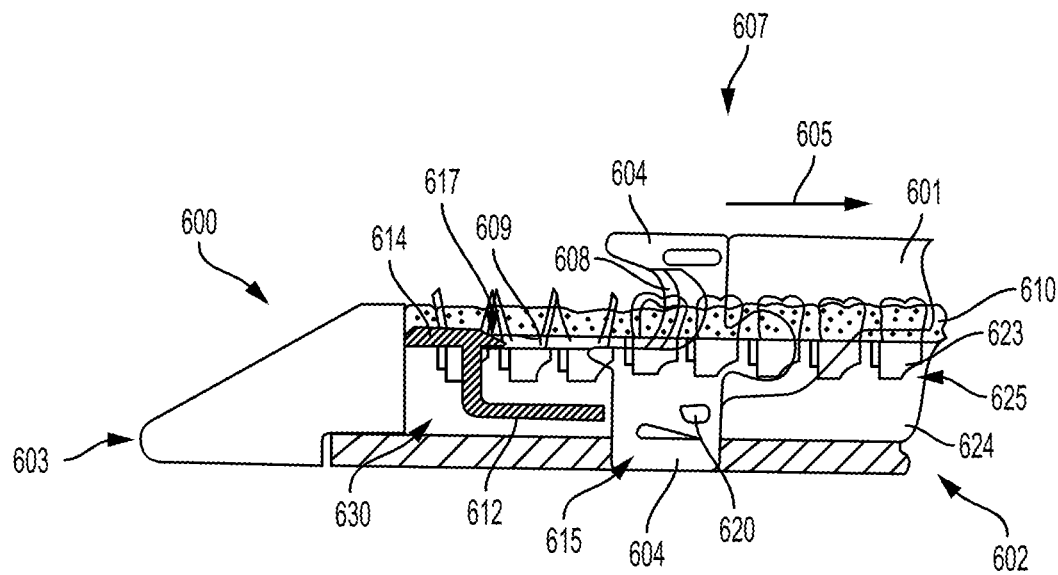
FIG. 7A is a side view of an embodiment of a jaw of an end effector, illustrating the jaw in a pre-fired configuration.
Figure 7B:
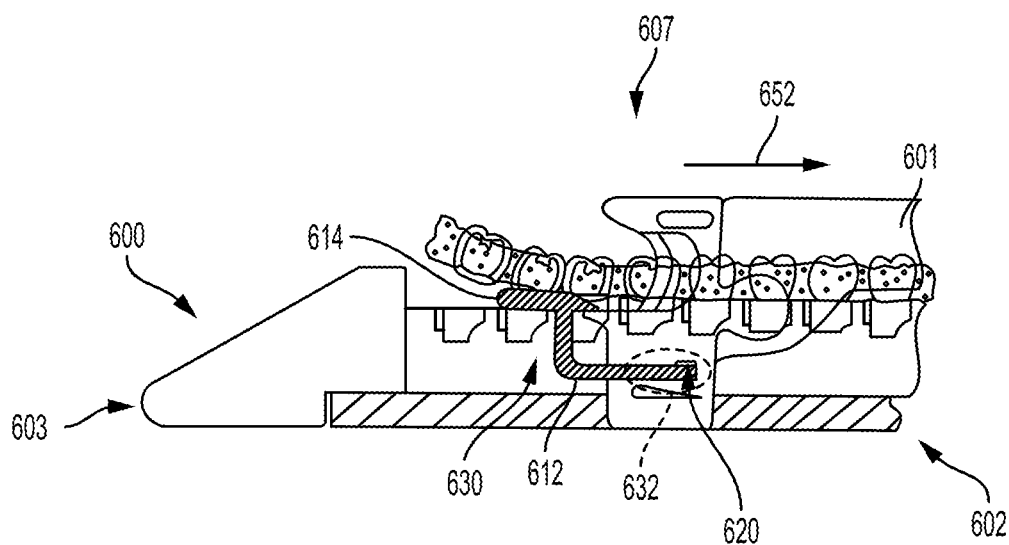
FIG. 7B is a side view of the jaw of FIG. 7A, illustrating the jaw in a fired configuration.

FIGS. 7A and 7B illustrate an example of a jaw 600 of an end effector 607. The end effector 607 can be coupled to a distal end of a shaft of a surgical stapling device (not shown). The end effector 607 can be used in any suitable surgical instrument, for example, a linear surgical stapler (e.g., stapler 10 in FIG. 1, stapler 50 in FIG. 4, or any other surgical stapler, including a circular stapler, such as stapler 80 in FIG. 5) which can be suitable for use with at least one adjunct.

The end effector 607, shown partially in FIGS. 7A and 7B, has a first jaw having a cartridge with a plurality of staple cavities configured to seat staples therein, the staple cavities opening on a tissue-facing surface of the cartridge. For example, the end effector 607 includes the jaw 600 in the form of cartridge having a plurality of staple cavities 625 configured to seat staples 623 therein. The staple cavities 623 open on a tissue-facing surface 609 of the cartridge 600. Although not shown in FIGS. 7A and 7B, the end effector 607 also includes a second jaw opposing the first jaw in the form of the cartridge 600 and having an anvil with a plurality of staple forming cavities formed on a tissue-facing surface thereof. The first and second jaws are configured to clamp tissue therebetween.

The end effector 607 also includes an implantable adjunct material releasably retained on at least one of the first and second jaws. In particular, in this example, the jaw 600 has an adjunct material or adjunct 610 releasably retained on the tissue facing surface 609 thereof. Although the jaw 600 is also referred to herein as a cartridge, it should be appreciated that the jaw 600 can have a staple channel configured to support a staple cartridge, which can be removably and replaceably seated within the staple channel. In some embodiments, the cartridge 600 can be part of a disposable loading unit coupled distally to a shaft of a surgical instrument. The cartridge 600 can be part of a cartridge reload assembly that is pre-assembled with an adjunct material. In such embodiments, a suitable adjunct loader can be used to attach an adjunct material to an anvil.

As shown in FIGS. 7A and 7B, the cartridge 600 includes a firing bar 601 configured to move longitudinally between a proximal end 602 and a distal end 603 of the cartridge 600. The firing bar 601 moves within a knife channel 624 formed in the cartridge 600 that extends longitudinally along the cartridge 600 and guides the motion of the firing bar 601 between the proximal and distal ends 602, 603. The knife channel 624 can extend through a cartridge in the lower jaw. In the illustrated example, the firing bar 601 is configured to move between an unfired position at the proximal end 602 of the end effector 607 and a fired position at the distal end 603 of the end effector 607.

The firing bar 601 can have a variety of configurations. For example, in the illustrated embodiment, the firing bar 601 includes at least one of a knife 608 and a staple driving assembly 615 configured to cause the staples 625 to fire from the staple cavities 623 against the staple forming cavities in the anvil (not shown). The distal end of the firing bar 601 includes a distal guide 604. It should be appreciated that the firing bar 601 can have any other components additionally or alternatively.

In use, when tissue is clamped between the jaw 600 with the adjunct 610 and the anvil of the end effector 607, as the firing bar 601 moves from the unfired position to the fired position, the knife 608 cuts through the adjunct 610. During this motion, the guide 604 can engage a wedge sled (not shown) that pushes the staples 625 held in the staple cavity 623 upwards towards an upper jaw (not shown) of the stapling device. In the process, the staples 625 can pass through the adjunct 610 and the tissue into the anvil of the upper jaw that faces the tissue. When the first and the second jaws clamp on the tissue, the staple forming cavities of the anvil guide the staples and cause the tissue and the adjunct 610 to be stapled together.

The adjunct 610 can be releasably retained on the tissue-facing surface 609 of the cartridge 600. The adjunct 610 can be coupled to the tissue facing surface 609 in various manners. For example, one or more adhesives (e.g., polydioxanone (PDS), CA, etc.) can be applied between the adjunct 610 and the tissue-facing surface 609 to releasably retain the adjunct 610 on the cartridge 600. In some embodiments, a backing layer made, e.g., of a PDS film, can be used to couple the adjunct 610 to the jaw 600. The backing layer can include one or more attachment points or portions (e.g., similar to the portions 506, 508 in FIG. 6A) that can be formed from an adhesive configured to be transitioned to an adhering state under application of heat. In other words, the adhesive can be at least partially melted (using, e.g., a loader configured to apply heat), in which state it can be used to couple the adjunct 610 directly or via the PDS film to the jaw. When the attachment adhesive cools, it couples the adjunct 610 (e.g., at one or more portions) to the jaw 600 securely. Additionally or alternatively, various other features (e.g., additional polymer layer (s), attachment features, etc.) can be used to releasably couple the adjunct 610 to the jaw 600.

Regardless of the manner in which the adjunct 610 is coupled to the cartridge 600, the adjunct 610 is coupled to the cartridge 600 releasably, such that it is separated from the cartridge 600 to remain with the tissue after the tissue stapling and/or cutting is completed during a surgical procedure. In some embodiments, the adjunct 610 can be releasably coupled to the jaw 600 in a secure manner, such that the end effector can be manipulated as desired, without the risk of the adjunct 610 sliding or slipping off the jaw 600.

At the same time, such secure attachment can require certain actions to separate the adjunct 610 from the cartridge 600.

Accordingly, in the illustrated embodiments, the end effector 607 includes an adjunct removal assembly 630 configured to separate the adjunct 610 from the cartridge 600. The adjunct removal assembly 630 is configured to couple to and move with the firing bar 601 to separate the adjunct material 610 from the end effector 607 as the firing bar 601 having the adjunct removal assembly 630 coupled thereto is returned from the fired position to the unfired position, as discussed in more detail below. For example, as the adjunct removal assembly 630 is moved proximally with the firing bar after the assembly is engaged by the firing bar, the adjunct removal assembly 630 can break or crack attachment points (formed, e.g., by a hot-melt adhesive) between the adjunct 610 and the cartridge 600. In this way, the adjunct 610 is separated from the cartridge.

As shown in FIGS. 7A and 7B, the adjunct removal assembly 630 is disposed at the distal end 603 of the cartridge 600. The adjunct removal assembly 630 is operably associated with the cartridge 600. As shown in FIG. 7A, it can be disposed at the distal end 603 of the end effector 607 in a configuration in which the assembly 630 is not coupled to the firing bar 601 when the surgical stapling device is in a pre-fired configuration. The adjunct removal assembly 630 can reside in the cartridge 600 and it can move longitudinally along the knife channel 624. In use, as the firing bar 601 moves from the unfired position at the proximal end 603 of the end effector 607 to the fired position at the distal end 602 of the end effector 607, as shown by an arrow 605 in FIG. 7A, the adjunct removal assembly 630 couples to firing bar 601 as discussed in more detail below. This movement results in the knife 608 cutting tissue disposed between the jaw 600 and the anvil (not shown). When the firing bar 601 moves proximally from the fired position to the unfired position, as shown by an arrow 652 in FIG. 7B, the adjunct removal assembly 630 coupled thereto moves with the firing bar 601.

The adjunct removal assembly 630 can have a variety of configurations. In the example illustrated, the assembly 630 includes an adjunct removal feature 614 and a mating feature 612. The adjunct removal feature 614, which can have various configurations, is configured to separate the adjunct 610 coupled to the jaw 600 from the jaw. The mating feature 612 is configured to mate with a respective mating feature 620 included in the firing bar 601 when the firing bar 601 is actuated to achieve the firing position.

As shown in FIG. 7A, in a pre-fired configuration of the end effector 607, the adjunct removal feature 614 is configured to be placed between the tissue-facing surface 609 and the adjunct 610. As also shown, a leading edge 617 of the adjunct removal feature 614 is disposed between the tissue-facing surface 609 and the adjunct 610. When the firing bar 601 has moved to the fired position and couples in this position to the adjunct removal assembly 630, and then moves proximally to return to the per-fired configuration, the adjunct removal feature 614 slides between the adjunct 610 and the tissue facing surface 609 thereby separating the adjunct 610 from the jaw 600, as shown in FIG. 7B. The leading edge 617 of the adjunct removal feature 614 facilitates separation of the adjunct 610 from the jaw 600. FIG. 7B shows the assembly 630 coupled to the firing bar 601 being pulled by the firing bar 601 towards the proximal end 602 of the end effector 607. As the adjunct removal feature 614 slides, it causes the adjunct 610 to separate from the tissue facing surface 609 of the jaw 600.

The mating feature 612 of the assembly 630 is configured to mate with the mating feature 620 of the firing bar 601. The mating features 612, 620 can be complementary to one another. For example, the mating feature 612 of the assembly 630 can be in the form of one or more protrusions, whereas the mating feature 620 of the firing bar 601 can be in the form of one or more openings or cavities configured to mate with the protrusion(s). The protrusions configured to mate with the cavity in the firing bar can include, e.g., a pair of bars disposed such that the firing bar sits between the bars when the adjunct removal assembly 630 is coupled to and moves with the firing bar. In particular, the bars can have a gap between them, as shown, for example, in FIG. 8 (pair of bars 714a, 714b). In use, the distal end of the firing bar 601 can slide into the gap between the pair of bars of the mating feature 612. FIG. 7B illustrates schematically (a circle 632) the mating feature 612 of the assembly 630 coupled to the mating feature 620 of the firing bar 601. For example, the bars are snapped into the mating feature 620 (e.g., a cavity), which can be assisted by mating elements or features that can be formed on the bars.

An example of a surgical method in accordance with the described techniques includes actuating the firing bar 601 so as to move it from an unfired position at the proximal end of the end effector to the fired position in the distal end of the end effector. The adjunct removal assembly 630 is engaged with the firing bar 601 when the firing bar 601 is in the fired position, and the firing bar 601 is actuated to return it from the fired position to the unfired position such that, as the firing bar 601 is actuated to return to the unfired position, the adjunct removal assembly 630 is moved with the fired bar 601 and thereby causes the adjunct material 610 releasably retained on the jaw 600 to be separated from that jaw.

It should be appreciated that the adjunct removal assembly 630 is shown in FIGS. 7A and 7B to be operatively coupled to the cartridge 600 by way of example only. Thus, in some implementations, an adjunct can be attached to a tissue-facing surface of a jaw of the surgical stapling device having an anvil. In such implementations, the adjunct removal assembly can be configured to be operatively coupled to the anvil such that it can slide longitudinally with a firing bar to separate the adjunct from a tissue-facing surface of the anvil. It should be appreciated that the adjunct may not be entirely removed from the jaw until the jaws are unclamped. Thus, the adjunct can be associated with the jaw (e.g., held against the jaw, albeit not coupled to the jaw) until the jaws are unclamped. Once the jaws are separated, the adjunct can be fully separated therefrom.

Figure 8:
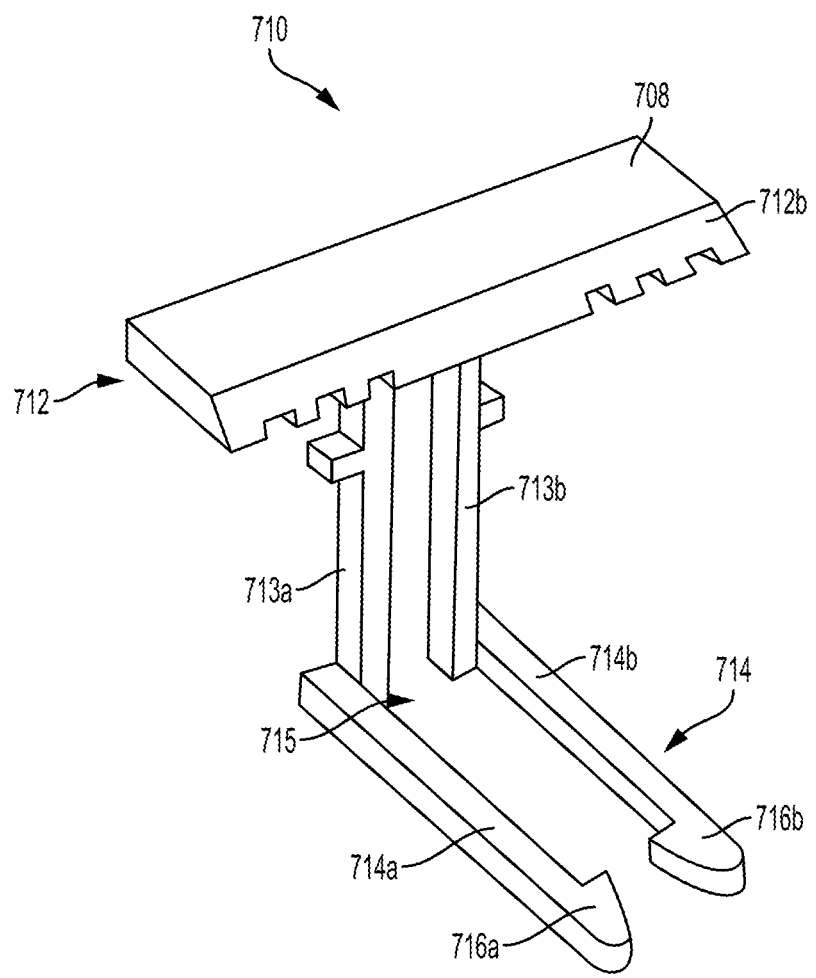
FIG. 8 illustrates a perspective view of an example of an adjunct removal system.

An adjunct removal assembly used to separate an adjunct material from a jaw of an end effector in accordance with the described techniques can have a variety of configurations. FIG. 8 illustrates an example of a portion of an adjunct removal system or assembly 710. The adjunct removal assembly 710 can be similar, for example, to adjunct removal assembly 630 in FIGS. 7A and 7B. The adjunct removal assembly 710 includes a stripper plate 712, a mating feature 714, and a pair of posts 713a, 713b coupling the stripper plate 712 to the mating feature 714. The stripper plate 712 serves as an adjunct removal feature, and it can have various configurations. In this example, it is generally rectangular, includes an adjunct-facing surface 708 and a leading surface 712b disposed at an angle with respect to the surface 708 and having a sharp leading edge that can facilitate the removal of the adjunct from the tissue facing surface of the cartridge. The adjunct-facing surface 708 is configured to have an adjunct disposed thereon.

As shown in FIG. 8, the stripper plate 712 is coupled to the pair of elongate posts 713a, 713b that can be attached to a mid-portion or approximately mid-portion of a side of the stripper plate 712 that is opposed to the adjunct-facing surface 708. The mating feature 714 also includes a pair of bars 714a, 714b extending from the ends of the posts 713a, 713b, respectively, that are opposed to the ends of the posts coupled to the stripper plate 712. As shown in FIG. 8, the bars 714a, 714b extend from the posts 713a, 713b such that the bars 714a, 714b form a gap 715 therebetween. As shown in FIG. 8, the posts 713a, 713b also include a gap therebetween, and the gap 715 can extend between the posts 713a and 713b. The bars 714a and 714b include mating features 716a, 716b, respectively (e.g., in the form of hooks facing one another), which can slide into a cavity in the distal end of the firing bar (not shown). As the distal end of the firing bar slides between the mating feature 714 (into the gap 715), it can push the bars 714a, 714b in an outward lateral direction. This can generate stress in the inward lateral direction that can cause the hook features 716a, 16b to snap inwards into the cavity in the distal end of the firing bar. The mating feature 714 can also guide the adjunct removal assembly 710 through the knife channel as the adjunct removal system slides longitudinally with the firing bar.

Figure 9:
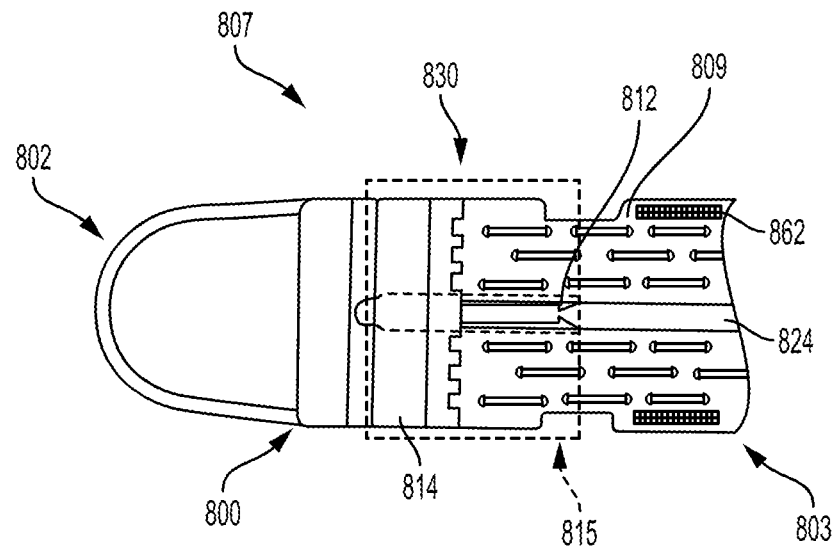
FIG. 9 illustrates a top-down view of a jaw of an end effector.

FIG. 9 illustrates a top view of an example of a jaw 800 of an end effector 807 that can be coupled to a suitable surgical stapler device (not shown). The jaw 800 is in the form of a cartridge and it can have an adjunct (not shown) removably coupled thereto. The jaw 700 can be similar to jaw 600 in FIGS. 7A and 7B and is therefore not described in detail. The end effector 807 includes an adjunct removal assembly 830, shown schematically within a dashed area 815, that can be similar to adjunct removal assembly 830 shown in FIGS. 7A and 7B. Thus, as shown in FIG. 9, the adjunct removal assembly 830 includes an adjunct removal feature 814 and a mating feature 812 configured to mate with a corresponding mating feature of a firing bar (not shown) when the firing bar is actuated to achieve a firing position.

The adjunct removal feature 814 is shown disposed along a tissue-facing surface 809 of the cartridge 800. The mating feature 812 of the of the adjunct removal assembly 830 can guide the assembly 830 along a knife channel 824 when the adjunct removal assembly 830 is coupled to and moved with the firing bar from a distal end 802 to a proximal end 803 of the end effector 807. As shown by way of example only, the tissue-facing surface 809 of the jaw 800 can include features (e.g., rough surfaces 862) that can facilitate attachment of the adjunct (not shown) to the jaw 800. For example, the rough surfaces 862 can provide traction to the adjunct and can thus allow an adhesive layer (which can have various features) between the adjunct and the surface 809 to form a stronger bond.

Figure 10:
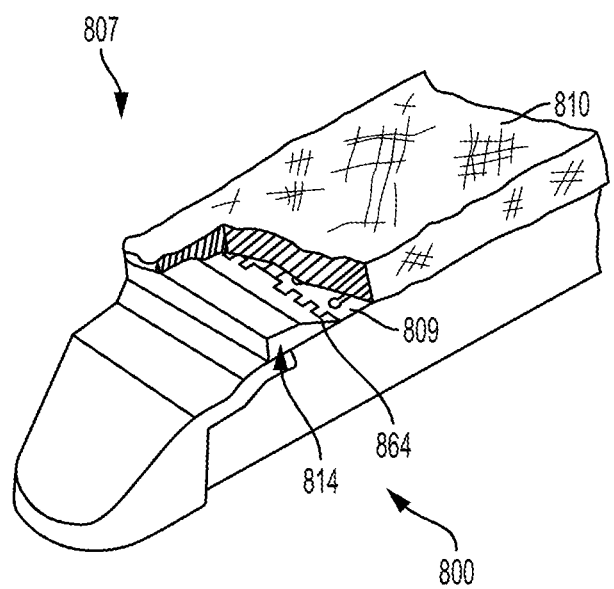
FIG. 10 illustrates a perspective, partially cut-away view of the jaw of the end effector of FIG. 9.

FIG. 10 illustrates the cartridge 800 with an adjunct 810 removably retained thereon. The adjunct removal assembly 830 is shown partially and FIG. 10 illustrates a relative orientation of adjunct 810 and the adjunct removal feature 814 of the adjunct removal assembly 830. In particular, in a pre-fired configuration of the end effector 807, the adjunct removal feature 814 is disposed between the jaw 800 and the adjunct 810. As illustrated, the adjunct removal feature 814 has a sharp leading edge 864 that can scrape the adjunct 810 from the tissue facing surface 809 of the cartridge 800. As discussed above, in a fired configuration, the adjunct removal assembly couples to and moves with a firing bar (not shown) to separate the adjunct material from the cartridge 800 as the firing bar having the adjunct removal assembly coupled thereto is returned from the fired position to the unfired position.

It should be appreciated that, an adjunct material can be releasably coupled to at least one jaw of an end effector using various techniques. For example, as mentioned above, the adjunct material can be coupled to the jaw using an adhesive configured to transition from a non-adhering state to an adhering state under application of heat. Non-limiting examples of the systems that can be used to releasably couple the adjunct material to a jaw of an end effector are described in a U.S. patent application Ser. No. 15/436,328 entitled "Systems for Coupling Adjuncts to an End Effector" and filed on Feb. 17, 2017, the content of which is incorporated by reference herein in its entirety.

It should also be appreciated that an adjunct removal assembly operatively coupled to an end effector can have a variety of configurations. For example, in some embodiments, the adjunct removal assembly can include a cutting element, such as a suture, string, or wire, that is "picked up" by a firing bar (e.g., by a knife) as the firing bar returns to an unfired position. As adjunct removal assembly is moved proximally with the returning firing bar, the cutting element separates the adjunct from the jaw.

A person skilled in the art will appreciate that the present disclosure has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical stapling device, comprising:
   a first jaw of an end effector having a cartridge with a plurality of staple cavities configured to seat staples therein, the staple cavities opening on a tissue-facing surface of the cartridge;
   a second jaw of the end effector opposing the first jaw and having an anvil with a plurality of staple forming cavities formed on a tissue-facing surface thereof, wherein the first and second jaws are configured to clamp tissue therebetween;
   an adjunct material releasably retained on at least one of the first and second jaws;

a firing bar configured to move between an unfired position at a proximal end of the end effector and a fired position at a distal end of the end effector,
wherein the firing bar includes at least one of a knife and a staple driving assembly configured to cause the staples to fire from the staple cavities against the staple forming cavities; and
an adjunct removal assembly configured to couple to and move with the firing bar to separate the adjunct material from the surgical stapling device as the firing bar having the adjunct removal assembly coupled thereto is returned from the fired position to the unfired position.

2. The surgical stapling device of claim 1, wherein the adjunct removal assembly is disposed at the distal end of the end effector in a configuration in which it is not coupled to the firing bar when the surgical stapling device is in a pre-fired configuration.

3. The surgical stapling device of claim 1, wherein the adjunct removal assembly is configured to move longitudinally along a knife channel in the cartridge.

4. The surgical stapling device of claim 1, wherein
the firing bar includes a first mating feature,
the adjunct removal assembly includes an adjunct removal feature and a second mating feature configured to mate with the first mating feature when the firing bar is actuated to achieve the firing position; and
the adjunct removal assembly is configured to move with the firing bar when the second mating feature is mated with the first mating feature such that, as the adjunct removal assembly is moved with the firing bar, the adjunct removal feature separates the adjunct material from one of the first and second jaws.

5. The surgical stapling device of claim 4, wherein the adjunct removal assembly is operably associated with the cartridge.

6. The surgical stapling device of claim 4, wherein the adjunct removal feature comprises a plate configured to slide between the adjunct material and one of the first jaw and the second jaw.

7. The surgical stapling device of claim 4, wherein the first mating feature comprises a cavity in the firing bar.

8. The surgical stapling device of claim 7, wherein the second mating feature comprises at least one protrusion configured to mate with the cavity in the firing bar.

9. The surgical stapling device of claim 8, wherein the at least one protrusion comprises a pair of bars disposed such that the firing bar sits between the bars when the adjunct removal assembly is coupled to and moves with the firing bar.

10. A surgical method, comprising:
actuating a firing bar of an end effector comprising a first jaw having a cartridge with a plurality of staple cavities configured to seat staples therein and a second jaw opposing the first jaw and having an anvil with a plurality of staple forming cavities formed on a tissue-facing surface thereof, wherein the first and second jaws are configured to clamp tissue therebetween, wherein the firing bar is actuated so as to be moved from an unfired position at a proximal end of the end effector to a fired position in a distal end of the end effector, and wherein the firing bar includes at least one of a knife and a staple driving assembly configured to cause the staples to fire from the staple cavities against the staple forming cavities;
engaging an adjunct removal assembly of the end effector with the firing bar when the firing bar is in the fired position;
actuating the firing bar to return it from the fired position to the unfired position such that, as the firing bar is actuated to return to the unfired position, the adjunct removal assembly is moved with the fired bar and thereby causes an adjunct material releasably retained on at least one of the first and second jaws to be separated from the at least one jaw.

11. The surgical method of claim 10, wherein the adjunct removal assembly is disposed at the distal end of the end effector in a configuration in which it is not coupled to the firing bar when the surgical stapling device is in a pre-fired configuration.

12. The surgical method of claim 10, wherein the firing bar includes a first mating feature, and engaging the adjunct removal assembly of the end effector with the firing bar comprises engaging a second mating feature of the adjunct removal assembly with the first mating feature.

13. The surgical method of claim 10, wherein the adjunct removal assembly is configured to move longitudinally along a knife channel in the cartridge.

* * * * *